United States Patent [19]
Wild et al.

[11] Patent Number: 6,130,318
[45] Date of Patent: Oct. 10, 2000

[54] HIL-4 MUTANT PROTEINS USED AS ANTAGONISTS OR PARTIAL AGONISTS OF HUMAN INTERLEUKIN 4

[75] Inventors: Hanno Wild, Wuppertal; Rudolf Hanko, Düsseldorf; Michael Dörschug, Heiligenhaus; Hans-Dietrich Hörlein, Wuppertal; Jürgen Beunink, Wuppertal; Heiner Apeler, Wuppertal; Hermann Wehlmann, Wuppertal; Walter Sebald, Würzburg, all of Germany

[73] Assignee: Bayer Aktiengellschaft, Germany

[21] Appl. No.: 08/765,012

[22] PCT Filed: Jun. 19, 1995

[86] PCT No.: PCT/EP95/02358

§ 371 Date: Dec. 19, 1996

§ 102(e) Date: Dec. 19, 1996

[87] PCT Pub. No.: WO96/01274

PCT Pub. Date: Jan. 18, 1996

[30] Foreign Application Priority Data

Jul. 1, 1994 [DE] Germany .............................. 44 23 131

[51] Int. Cl.$^7$ .......................... C07K 14/54; A61K 38/20
[52] U.S. Cl. ........................ 530/351; 424/85.1; 424/85.2
[58] Field of Search .......................... 530/351; 424/85.2, 424/85.1

[56] References Cited

U.S. PATENT DOCUMENTS

| | | |
|---|---|---|
| 3,773,919 | 11/1973 | Boswell et al. . |
| 4,179,337 | 12/1979 | Davis et al. . |
| 4,301,144 | 11/1981 | Iwashita et al. . |
| 4,485,045 | 11/1984 | Regen . |
| 4,496,689 | 1/1985 | Mitra . |
| 4,544,545 | 10/1985 | Ryan et al. . |
| 4,590,060 | 5/1986 | Ehrenfeld . |
| 4,615,885 | 10/1986 | Nakagame et al. . |
| 4,619,794 | 10/1986 | Hauser . |
| 4,640,835 | 2/1987 | Shimizu et al. . |
| 4,670,417 | 6/1987 | Iwasaki et al. . |
| 4,791,192 | 12/1988 | Nakagawa et al. . |
| 5,013,556 | 5/1991 | Woodle et al. . |
| 5,298,410 | 3/1994 | Phillips et al. . |
| 5,538,884 | 7/1996 | Dörreich et al. . |
| 5,723,118 | 3/1998 | Sebald ..................................... 530/351 |
| B1 4,767,628 | 7/1990 | Hutchinson . |

FOREIGN PATENT DOCUMENTS

| | | |
|---|---|---|
| 36 676 | 9/1981 | European Pat. Off. . |
| 52 322 | 5/1982 | European Pat. Off. . |
| 102 324 | 3/1984 | European Pat. Off. . |
| 133 988 | 3/1985 | European Pat. Off. . |
| 32 18 121 | 11/1983 | Germany . |
| WO 87/05330 | 9/1987 | WIPO . |
| WO 88/04667 | 6/1988 | WIPO . |
| WO 89/02922 | 4/1989 | WIPO . |
| WO 93/10235 | 5/1993 | WIPO . |

OTHER PUBLICATIONS

Muller et al, *J Mol Biol* 1995, p 360–72, vol. 247.
Morrison et al, *JBC* 267 (17) 1992, p 11957–63.
Powers et al, *Science* 256, Jun. 1992, p 1673–77.
Kruse et al *EMBO* 12(13) 1993, p 5121–29.
Tony et al, *Eur J Bioch* 1994.
Francis, Forms of Growth Factors, vol. 3, May, 1992, p 4–10.
Kruse et al *EMBO* 11(9) 1992, p 3237–44.
George et al. Macro Molecular Sequenc Y & Synthesis Selected Method & Application 1988, p 127–145.
Ngo et al, The Protein Folding & Tiertiary Structure Prediction, ed Merz et al, 1994, p 433.
Bowie et al, Science 247, 1990, p 1306–10.
Frömmel et al, *J. Mol. Eval* 1985, p 235–57, vol 21.
Kruse et al, (1991) FEBS Lett. 286, 58–60.
Kikutani et al, (1986) Cell 47, 657–665.
Yokota et al, (1986) Proc.Natl.Acad.Sci., USA 83, 5894–5898.
Carr et al, Biochemistry 1991, 30 1515–1523.
Weigel et al, (1989) Eur.J.Biochem. 180, 295–300.
Flinta et al, Eur.J.Biochem. 154, 193–196 (1986).
Cunningham et al, Science, 244, 1081–1085 (1989).
Aplin et al, CRC Crit.Rev.Biochem., 259–306 (1981).
Hakkimuddin et al, Arch.Biochem.Biophys., 259:52 (1987).
Edge et al, Anal.Biochem., 118:131 (1981).
Win Ping Deng et al, Anal.Biochem. 200:81 (1992).
Thotakura et al, Meth.Enzymol. 138:350 (1987).
Duksin et al, J.Biol.Chem., 257:3105 (1982).
Maxfield et al, Polymer 16:505–509 (1975).
Bailey et al, Nonionic surfactants [Schick, M.J., Hrsq.] 794–821 (1967).
Abuchowski et al, J.Biol.Chem. 252:3582–3586 and 3578–3581 (1977).
Abuchowski et al, Cancer Biochem.Biophys., 7:175–186 (1984).
Katre et al, Proc.Natl. Acad.Sci., 84:1487–1491 (1987).
Goodson et al, Biotechnology, 8:343–346 (1990).
Remington's Pharmaceutical Sciences, 16. Auflage, Osol A., Hrsg. (1980) (Complete Book).
Langer et al, J.Biomed.Mater.Res., 15:267–277 (1981).
Sidman et al, Biopolymers, 22:547–556 (1983).
Eppstein et al, Proc.Natl.Acad.Sci. USA, 82:3688–3692 (1985).
Hwang et al, Proc.Natl.Acad.Sci. USA, 77:4030–4034 (1980).
Kruse et al, EMBO J. 11, 3237 (1992).
Kruse et al, EMBO J. 11, 789–790 (1992).

*Primary Examiner*—Garnette D. Draper
*Attorney, Agent, or Firm*—Norris McLaughlin & Marcus

[57] ABSTRACT

The present invention relates to novel hIL-4 mutant proteins, to processes for preparing them, and to their use as medicaments, in particular in overshooting, falsely regulated immune reactions and autoimmune diseases.

12 Claims, 1 Drawing Sheet

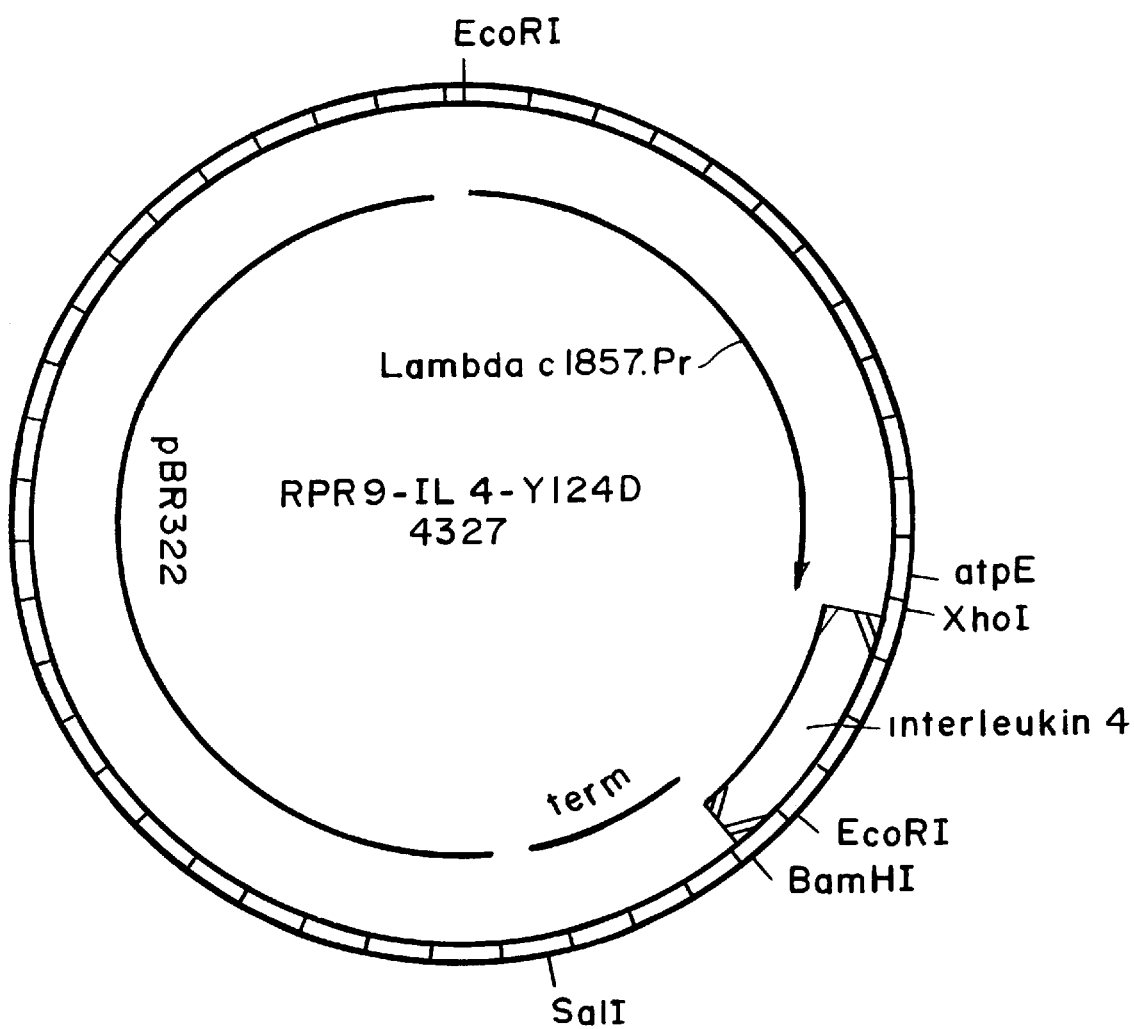

```
                       SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
           (A) LENGTH: 16 base pairs
           (B) TYPE: nucleic acid
           (C) STRANDEDNESS: single
           (D) TOPOLOGY: linear (ii) MOLECULE TYPE: cDNA (iii) HYPOTHETICAL: no (iv) ANTI-SENSE: no (vi) ORIGINAL SOURCE:
           (C) INDIVIDUAL ISOLATE: synthetic (xi) SEQUENCE DESCRIPTION:  SEQ ID NO: 1:

CATGCACAAG TGCGAT                                                   16

(2) INFORMATION FOR SEQ ID NO: 2:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: cDNA (iii) HYPOTHETICAL: no (iv) ANTI-SENSE: no (vi) ORIGINAL SOURCE:
           (C) INDIVIDUAL ISOLATE: synthetic (xi) SEQUENCE DESCRIPTION:  SEQ ID NO: 2:

ATCGCACTTG TG                                                       12

(2) INFORMATION FOR SEQ ID NO: 3:

(i) SEQUENCE CHARACTERISTICS:
           (A) LENGTH: 21 base pairs
           (B) TYPE: nucleic acid
           (C) STRANDEDNESS: single
```

```
            (D) TOPOLOGY: linear (ii) MOLECULE TYPE: cDNA (iii) HYPOTHETICAL: no (iv) ANTI-SENSE: no (vi) ORIGINAL SOURCE:
            (C) INDIVIDUAL ISOLATE: synthetic (xi) SEQUENCE DESCRIPTION: SEQ ID NO: 3:

GCCTCCAAGG ACACAACTGA G                                           21

(2) INFORMATION FOR SEQ ID NO: 4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: no (iv) ANTI-SENSE: no (vi) ORIGINAL SOURCE:
            (C) INDIVIDUAL ISOLATE: synthetic (xi) SEQUENCE DESCRIPTION: SEQ ID NO: 4:

GTGAAGGAAG CCGACCAGAG TACG                                        24

(2) INFORMATION FOR SEQ ID NO: 5:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: no (iv) ANTI-SENSE: no (vi) ORIGINAL SOURCE:
            (C) INDIVIDUAL ISOLATE: synthetic (xi) SEQUENCE DESCRIPTION: SEQ ID NO: 5:

CTGGAGACTG CCATGGCCCA CAAGTGCGAT ATCACC                           36

(2) INFORMATION FOR SEQ ID NO: 6:

(i) SEQUENCE CHARACTERISTICS:
            (A) LENGTH: 131 amino acids
            (B) TYPE: amino acid
            (D) TOPOLOGY: linear (xi) SEQUENCE DESCRIPTION: SEQ ID NO: 6:

Met Ala His Lys Cys Asp Ile Thr Leu Gln Glu
 1               5

Ile Ile Lys Thr Leu Asn Ser Leu Thr Glu
10              15

Gln Lys Thr Leu Cys Thr Glu Leu Thr Val
20              25

Thr Asp Ile Phe Ala Ala Ser Lys Asn Thr
30              35
```

```
Thr Glu Asn Glu Thr Phe Cys Arg Ala Ala
40                  45

Thr Val Leu Arg Gln Phe Tyr Ser His His
50                  55

Glu Lys Asp Thr Arg Cys Leu Gly Ala Thr
60                  65

Ala Gln Gln Phe His Arg His Lys Gln Leu
70                  75

Ile Arg Phe Leu Lys Arg Leu Asp Arg Asn
80                  85

Leu Trp Gly Leu Ala Gly Leu Asn Ser Cys
90                  95

Pro Val Lys Glu Ala Asn Gln Ser Thr Leu
100                 105

Glu Asn Phe Leu Glu Arg Leu Lys Thr Ile
110                 115

Met Arg Glu Lys Asp Ser Lys Cys Ser Ser
120                 125

(2) INFORMATION FOR SEQ ID NO: 7:

(i) SEQUENCE CHARACTERISTICS:
        (A) LENGTH: 131 amino acids
        (B) TYPE: amino acid
        (D) TOPOLOGY: linear (xi) SEQUENCE DESCRIPTION:  SEQ ID NO: 7:
Met Ala His Lys Cys Asp Ile Thr Leu Gln Glu
            1               5

Ile Ile Lys Thr Leu Asn Ser Leu Thr Glu
10                  15

Gln Lys Thr Leu Cys Thr Glu Leu Thr Val
20                  25

Thr Asp Ile Phe Ala Ala Ser Lys Asn Thr
30                  35

Thr Glu Asn Glu Thr Phe Cys Arg Ala Ala
40                  45

Thr Val Leu Arg Gln Phe Tyr Ser His His
50                  55

Glu Lys Asp Thr Arg Cys Leu Gly Ala Thr
60                  65

Ala Gln Gln Phe His Arg His Lys Gln Leu
70                  75

Ile Arg Phe Leu Lys Arg Leu Asp Arg Asn
80                  85

Leu Trp Gly Leu Ala Gly Leu Asn Ser Cys
90                  95

Pro Val Lys Glu Ala Asn Gln Ser Thr Leu
100                 105

Glu Asn Phe Leu Glu Arg Leu Lys Thr Ile
110                 115

Met Asp Glu Lys Asp Ser Lys Cys Ser Ser
120                 125

(2) INFORMATION FOR SEQ ID NO: 8:

(i) SEQUENCE CHARACTERISTICS:
```

(A) LENGTH: 131 amino acids
        (B) TYPE: amino acid
        (D) TOPOLOGY: linear (xi) SEQUENCE DESCRIPTION: SEQ ID NO: 8:

Met Ala His Lys Cys Asp Ile Thr Leu Gln Glu
        1               5

Ile Ile Lys Thr Leu Asn Ser Leu Thr Glu
10                  15

Gln Lys Thr Leu Cys Thr Glu Leu Thr Val
20                  25

Thr Asp Ile Phe Ala Ala Ser Lys Asn Thr
30                  35

Thr Glu Asn Glu Thr Phe Cys Arg Ala Ala
40                  45

Thr Val Leu Arg Gln Phe Tyr Ser His His
50                  55

Glu Lys Asp Thr Arg Cys Leu Gly Ala Thr
60                  65

Ala Gln Gln Phe His Arg His Lys Gln Leu
70                  75

Ile Arg Phe Leu Lys Arg Leu Asp Arg Asn
80                  85

Leu Trp Gly Leu Ala Gly Leu Asn Ser Cys
90                  95

Pro Val Lys Glu Ala Asn Gln Ser Thr Leu
100                 105

Glu Asn Phe Leu Glu Arg Leu Lys Thr Ile
110                 115

Met Asp Glu Lys Asp Asp Lys Cys Ser Ser
120                 125

(2) INFORMATION FOR SEQ ID NO: 9:

(i) SEQUENCE CHARACTERISTICS:
        (A) LENGTH: 131 amino acids
        (B) TYPE: amino acid
        (D) TOPOLOGY: linear (xi) SEQUENCE DESCRIPTION: SEQ ID NO: 9:

Met Ala His Lys Cys Asp Ile Thr Leu Gln Glu
        1               5

Ile Ile Lys Thr Leu Asn Ser Leu Thr Glu
10                  15

Gln Lys Thr Leu Cys Thr Glu Leu Thr Val
20                  25

Thr Asp Ile Phe Ala Ala Ser Lys Asn Thr
30                  35

Thr Glu Asn Glu Thr Phe Cys Arg Ala Ala
40                  45

Thr Val Leu Arg Gln Phe Tyr Ser His His
50                  55

Glu Lys Asp Thr Arg Cys Leu Gly Ala Thr
60                  65

Ala Gln Gln Phe His Arg His Lys Gln Leu
70                  75

```
Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asn Gln Ser Thr Leu
100                 105

Glu Asn Phe Leu Glu Arg Leu Lys Thr Ile
110                 115

Met Arg Glu Lys Asp Asp Lys Cys Ser Ser
120                 125
```

(2) INFORMATION FOR SEQ ID NO: 10:

(i) SEQUENCE CHARACTERISTICS:
        (A) LENGTH: 131 amino acids
        (B) TYPE: amino acid
        (D) TOPOLOGY: linear (xi) SEQUENCE DESCRIPTION: SEQ ID NO: 10:

```
Met Ala His Lys Cys Asp Ile Thr Leu Gln Glu
         1                   5

Ile Ile Lys Thr Leu Asn Ser Leu Thr Glu
 10                  15

Gln Lys Thr Leu Cys Thr Glu Leu Thr Val
 20                  25

Thr Asp Ile Phe Ala Ala Ser Lys Asn Thr
 30                  35

Thr Glu Asn Glu Thr Phe Cys Arg Ala Ala
 40                  45

Thr Val Leu Arg Gln Phe Tyr Ser His His
 50                  55

Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asn Gln Ser Thr Leu
100                 105

Glu Asn Phe Leu Glu Arg Leu Lys Thr Ile
110                 115

Met Asp Glu Lys Tyr Asp Lys Cys Ser Ser
120                 125
```

(2) INFORMATION FOR SEQ ID NO: 11:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO: 11:

```
Met His Lys Cys Asp Ile Thr Leu Gln Glu
         1                   5

Ile Ile Lys Thr Leu Asn Ser Leu Thr Glu
 10                  15
```

Gln Lys Thr Leu Cys Thr Glu Leu Thr Val
 20                  25

Thr Asp Ile Phe Ala Ala Ser Lys Asp Thr
 30                  35

Thr Glu Asn Glu Thr Phe Cys Arg Ala Ala
 40                  45

Thr Val Leu Arg Gln Phe Tyr Ser His His
 50                  55

Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asp Gln Ser Thr Leu
 100                 105

Glu Asn Phe Leu Glu Arg Leu Lys Thr Ile
 110                 115

Met Arg Glu Lys Asp Ser Lys Cys Ser Ser
 120                 125

(2) INFORMATION FOR SEQ ID NO: 12:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO: 12:

Met His Lys Cys Asp Ile Thr Leu Gln Glu
  1                   5

Ile Ile Lys Thr Leu Asn Ser Leu Thr Glu
 10                  15

Gln Lys Thr Leu Cys Thr Glu Leu Thr Val
 20                  25

Thr Asp Ile Phe Ala Ala Ser Lys Asp Thr
 30                  35

Thr Glu Asn Glu Thr Phe Cys Arg Ala Ala
 40                  45

Thr Val Leu Arg Gln Phe Tyr Ser His His
 50                  55

Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asp Gln Ser Thr Leu
 100                 105

Glu Asn Phe Leu Glu Arg Leu Lys Thr Ile
 110                 115

```
Met Asp Glu Lys Asp Ser Lys Cys Ser Ser
120                 125
```

(2) INFORMATION FOR SEQ ID NO: 13:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO: 13:

```
Met His Lys Cys Asp Ile Thr Leu Gln Glu
  1             5

Ile Ile Lys Thr Leu Asn Ser Leu Thr Glu
 10             15

Gln Lys Thr Leu Cys Thr Glu Leu Thr Val
 20             25

Thr Asp Ile Phe Ala Ala Ser Lys Asp Thr
 30             35

Thr Glu Asn Glu Thr Phe Cys Arg Ala Ala
 40             45

Thr Val Leu Arg Gln Phe Tyr Ser His His
 50             55

Glu Lys Asp Thr Arg Cys Leu Gly Ala Thr
 60             65

Ala Gln Gln Phe His Arg His Lys Gln Leu
 70             75

Ile Arg Phe Leu Lys Arg Leu Asp Arg Asn
 80             85

Leu Trp Gly Leu Ala Gly Leu Asn Ser Cys
 90             95

Pro Val Lys Glu Ala Asp Gln Ser Thr Leu
100            105

Glu Asn Phe Leu Glu Arg Leu Lys Thr Ile
110            115

Met Asp Glu Lys Asp Asp Lys Cys Ser Ser
120            125
```

(2) INFORMATION FOR SEQ ID NO: 14:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO: 14:

```
Met His Lys Cys Asp Ile Thr Leu Gln Glu
  1             5

Ile Ile Lys Thr Leu Asn Ser Leu Thr Glu
 10             15

Gln Lys Thr Leu Cys Thr Glu Leu Thr Val
 20             25

Thr Asp Ile Phe Ala Ala Ser Lys Asp Thr
 30             35

Thr Glu Asn Glu Thr Phe Cys Arg Ala Ala
 40             45

Thr Val Leu Arg Gln Phe Tyr Ser His His
 50             55
```

```
Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asp Gln Ser Thr Leu
100                 105

Glu Asn Phe Leu Glu Arg Leu Lys Thr Ile
110                 115

Met Arg Glu Lys Asp Asp Lys Cys Ser Ser
120                 125

(2) INFORMATION FOR SEQ ID NO: 15:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO: 15:

Met His Lys Cys Asp Ile Thr Leu Gln Glu
     1            5

Ile Ile Lys Thr Leu Asn Ser Leu Thr Glu
 10                  15

Gln Lys Thr Leu Cys Thr Glu Leu Thr Val
 20                  25

Thr Asp Ile Phe Ala Ala Ser Lys Asp Thr
 30                  35

Thr Glu Asn Glu Thr Phe Cys Arg Ala Ala
 40                  45

Thr Val Leu Arg Gln Phe Tyr Ser His His
 50                  55

Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asp Gln Ser Thr Leu
100                 105

Glu Asn Phe Leu Glu Arg Leu Lys Thr Ile
110                 115

Met Asp Glu Lys Tyr Asp Lys Cys Ser Ser
120                 125

(2) INFORMATION FOR SEQ ID NO: 16:

(i) SEQUENCE CHARACTERISTICS:
        (A) LENGTH: 129 amino acids
        (B) TYPE: amino acid
        (D) TOPOLOGY: linear
```

(xi) SEQUENCE DESCRIPTION: SEQ ID NO: 16:

```
His Lys Cys Asp Ile Thr Leu Gln Glu
 1               5
Ile Ile Lys Thr Leu Asn Ser Leu Thr Glu
 10              15
Gln Lys Thr Leu Cys Thr Glu Leu Thr Val
 20              25
Thr Asp Ile Phe Ala Ala Ser Lys Asn Thr
 30              35
Thr Glu Asn Glu Thr Phe Cys Arg Ala Ala
 40              45
Thr Val Leu Arg Gln Phe Tyr Ser His His
 50              55
Glu Lys Asp Thr Arg Cys Leu Gly Ala Thr
 60              65
Ala Gln Gln Phe His Arg His Lys Gln Leu
 70              75
Ile Arg Phe Leu Lys Arg Leu Asp Arg Asn
 80              85
Leu Trp Gly Leu Ala Gly Leu Asn Ser Cys
 90              95
Pro Val Lys Glu Ala Asn Gln Ser Thr Leu
 100             105
Glu Asn Phe Leu Glu Arg Leu Lys Thr Ile
 110             115
Met Arg Glu Lys Asp Ser Lys Cys Ser Ser
 120             125
```

(2) INFORMATION FOR SEQ ID NO: 17:

(i) SEQUENCE CHARACTERISTICS:
        (A) LENGTH: 129 amino acids
        (B) TYPE: amino acid
        (D) TOPOLOGY: linear (xi) SEQUENCE DESCRIPTION: SEQ ID NO: 17:

```
His Lys Cys Asp Ile Thr Leu Gln Glu
 1               5
Ile Ile Lys Thr Leu Asn Ser Leu Thr Glu
 10              15
Gln Lys Thr Leu Cys Thr Glu Leu Thr Val
 20              25
Thr Asp Ile Phe Ala Ala Ser Lys Asn Thr
 30              35
Thr Glu Asn Glu Thr Phe Cys Arg Ala Ala
 40              45
Thr Val Leu Arg Gln Phe Tyr Ser His His
 50              55
Glu Lys Asp Thr Arg Cys Leu Gly Ala Thr
 60              65
Ala Gln Gln Phe His Arg His Lys Gln Leu
 70              75
Ile Arg Phe Leu Lys Arg Leu Asp Arg Asn
 80              85
Leu Trp Gly Leu Ala Gly Leu Asn Ser Cys
 90              95
```

```
Pro Val Lys Glu Ala Asn Gln Ser Thr Leu
100                 105

Glu Asn Phe Leu Glu Arg Leu Lys Thr Ile
110                 115

Met Asp Glu Lys Asp Ser Lys Cys Ser Ser
120                 125

(2) INFORMATION FOR SEQ ID NO: 18:

(i) SEQUENCE CHARACTERISTICS:
        (A) LENGTH: 129 amino acids
        (B) TYPE: amino acid
        (D) TOPOLOGY: linear (xi) SEQUENCE DESCRIPTION:   SEQ ID NO: 18:

His Lys Cys Asp Ile Thr Leu Gln Glu
 1                5

Ile Ile Lys Thr Leu Asn Ser Leu Thr Glu
10                  15

Gln Lys Thr Leu Cys Thr Glu Leu Thr Val
20                  25

Thr Asp Ile Phe Ala Ala Ser Lys Asn Thr
30                  35

Thr Glu Asn Glu Thr Phe Cys Arg Ala Ala
40                  45

Thr Val Leu Arg Gln Phe Tyr Ser His His
50                  55

Glu Lys Asp Thr Arg Cys Leu Gly Ala Thr
60                  65

Ala Gln Gln Phe His Arg His Lys Gln Leu
70                  75

Ile Arg Phe Leu Lys Arg Leu Asp Arg Asn
80                  85

Leu Trp Gly Leu Ala Gly Leu Asn Ser Cys
90                  95

Pro Val Lys Glu Ala Asn Gln Ser Thr Leu
100                 105

Glu Asn Phe Leu Glu Arg Leu Lys Thr Ile
110                 115

Met Asp Glu Lys Asp Asp Lys Cys Ser Ser
120                 125

(2) INFORMATION FOR SEQ ID NO: 19:

(i) SEQUENCE CHARACTERISTICS:
        (A) LENGTH: 129 amino acids
        (B) TYPE: amino acid
        (D) TOPOLOGY: linear (xi) SEQUENCE DESCRIPTION:   SEQ ID NO: 19:

His Lys Cys Asp Ile Thr Leu Gln Glu
 1                5

Ile Ile Lys Thr Leu Asn Ser Leu Thr Glu
10                  15

Gln Lys Thr Leu Cys Thr Glu Leu Thr Val
20                  25

Thr Asp Ile Phe Ala Ala Ser Lys Asn Thr
30                  35
```

```
Thr Glu Asn Glu Thr Phe Cys Arg Ala Ala
 40                  45

Thr Val Leu Arg Gln Phe Tyr Ser His His
 50                  55

Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asn Gln Ser Thr Leu
100                 105

Glu Asn Phe Leu Glu Arg Leu Lys Thr Ile
110                 115

Met Arg Glu Lys Asp Asp Lys Cys Ser Ser
120                 125

(2) INFORMATION FOR SEQ ID NO: 20:

(i) SEQUENCE CHARACTERISTICS:
        (A) LENGTH: 129 amino acids
        (B) TYPE: amino acid
        (D) TOPOLOGY: linear (xi) SEQUENCE DESCRIPTION: SEQ ID NO: 20:

His Lys Cys Asp Ile Thr Leu Gln Glu
 1                   5

Ile Ile Lys Thr Leu Asn Ser Leu Thr Glu
 10                  15

Gln Lys Thr Leu Cys Thr Glu Leu Thr Val
 20                  25

Thr Asp Ile Phe Ala Ala Ser Lys Asn Thr
 30                  35

Thr Glu Asn Glu Thr Phe Cys Arg Ala Ala
 40                  45

Thr Val Leu Arg Gln Phe Tyr Ser His His
 50                  55

Glu Lys Asp Thr Arg Cys Leu Gly Ala Thr
 60                  65

Ala Gln Gln Phe His Arg His Lys Gln Leu
 70                  75

Ile Arg Phe Leu Lys Arg Leu Asp Arg Asn
 80                  85

Leu Trp Gly Leu Ala Gly Leu Asn Ser Cys
 90                  95

Pro Val Lys Glu Ala Asn Gln Ser Thr Leu
100                 105

Glu Asn Phe Leu Glu Arg Leu Lys Thr Ile
110                 115

Met Asp Glu Lys Tyr Asp Lys Cys Ser Ser
120                 125
```

HIL-4 MUTANT PROTEINS USED AS ANTAGONISTS OR PARTIAL AGONISTS OF HUMAN INTERLEUKIN 4

BACKGROUND OF THE INVENTION

1. Field of the Invention

The present invention relates to novel hIL-4 mutant proteins, to processes for preparing them, and to their use as medicaments, in particular in association with overshooting, falsely regulated immune reactions and autoimmune diseases.

2. Description of Related Art

PCT WO 93/10235 already discloses therapeutic agents which are or which contain antagonists or partial agonists of hIL-4, with the antagonists or partial agonists being hIL-4 mutant proteins.

Human interleukin 4 hIL-4) is one of the many cytokines which induce and coordinate the proliferation, maturation, survival and differentiation of lymphoid and myeloid cells. In particular, hIL-4 is involved in the IgE-mediated immune reaction and directly accelerates the proliferation of thymocytes and activated T cells. A high-affinity IL-4 receptor protein of Mr 140,000 has been identified which, according to its cDNA sequence, consists of 800 amino acid residues. This protein belongs to a recently described group of receptors which are designated the haematopoietin receptor superfamily.

Based on the cloned cDNA, the amino acid sequence of the mature IL-4 consists of 129 residues. The cDNA has been expressed in *E. coli* and yeast. Recombinant IL-4 having high biological activity can be isolated from these sources.

Very recently, a monoclonal antibody has been disclosed which exhibits antagonistic properties towards human interleukin 4. This antibody contains a Fab fragment and is produced by a human/human hybridoma cell line. A hybridoma cell line from the spleen cells of a rat which was immunized against (non-)glycosylated human IL-4 also produces monoclonal antibodies against hIL-4.

The role of interleukin 4 in allergic processes provides grounds for hoping that substances which inhibit interleukin 4-mediated processes, or compete with hIL4, might interrupt the disease-triggering reaction chain.

DE 41 37 333 A1 describes hIL-4 mutant proteins in which the amino acid(s) occurring naturally in the wild type at one or more of positions 120, 121, 122, 123, 124, 125, 126, 127 or 128 has/have been replaced with one or more, respectively, of the other possible natural amino acids. These hIL-4 mutant proteins are antagonists or partial agonists of human IL-4.

SUMMARY OF THE INVENTION

The present invention now relates to novel hIL-4 mutant proteins which are antagonists or partial agonists of human interleukin 4 and in which further modifications of the hIL-4 protein have been carried out in addition to the replacement (s) at positions 121, 124 or 125. These modifications are carried out in order to increase the stability of the hIL-4 mutant proteins, in order to extend the biological half life or in order to facilitate the preparation and purification process.

For this, the amino acids which naturally occur in the wild type are deleted, or replaced by other amino acids, at one or more positions, or else additional amino acids are inserted, at the C terminus or at the N terminus as well, or else one or more of the amino acids is/are substituted by various non-protein polymers, for example polyethylene glycol and its derivatives, or by glycosyl residues.

Within the context of the invention, amino acids are generally
Ala L-alanine
Arg L-arginine
Asn L-asparagine
Asp L-aspartic acid
Cys L-cysteine
Gln L-glutamine
Glu L-glutamic acid
Gly L-glycine
His L-histidine
Ile L-isoleucine
Leu L-leucine
Lys L-lysine
Met L-methionine
Pro L-proline
Phe L-phenylalanine
Ser L-serine
Thr L-threonine
Trp L-tryptophan
Tyr L-tyrosine
Val L-valine,
with it being possible, for simplicity, to omit the configuration designation.

Non-protein polymers are understood, for example, as being polyethylene glycol, polypropylene glycol or polyoxyalkylenes, as described in U.S. Pat. Nos. 4,640,835, 4,496,689, 4,301,144, 4,670,417, 4,791,192 or 4,179,337.

Glycosylation is understood as being the linking of a carbohydrate skeleton to the side chain of an asparagine residue ("N-glycosylation") or the coupling of a sugar, preferably N-acetylgalactosamine, galactose or xylose to serine, threonine, 4-hydroxyproline or 5-hydroxylysine (O-glycosylation).

BRIEF DESCRIPTION OF THE DRAWINGS

The invention will now be described in more detail with reference to the drawing, wherein:

FIG. 1 is a map of vector RPR9-IL 4-Y124 4327.

DESCRIPTION OF THE PREFERRED EMBODIMENTS

Preference is given to hIL-4 mutant proteins in which amino acid 124 (tyrosine), amino acid 121 (arginine) and amino acid 125 (serine) are replaced, in any combination, with one of the possible natural amino acids and in which, in addition, the N terminus and/or C terminus of the molecule is/are modified and/or one or more polyethylene glycol molecules is/are covalently bonded to the molecule and/or glycosylation sites which are present in the molecule are partially or completely deleted.

Muteins in which amino acid 124 (tyrosine), amino acid 121 (arginine) and amino acid 125 (serine) are replaced, in any combination, with aspartic acid or glutamic acid, and in which, in addition, the N terminus and/or C terminus of the molecule is/are modified, and/or one or more polyethylene glycol molecules is/are covalently bonded to the molecule, and/or glycosylation sites which are present in the molecule are partially or completely deleted, are particularly preferred embodiments from this group.

Preferred embodiments are also those in which amino acids 121 (arginine) and 125 (serine) are replaced with a naturally occurring amino acid, preferably aspartic acid or glutamic acid, and in which, in addition, the N terminus and/or C terminus of the molecule is/are modified, and/or one or more polyethylene glycol molecules is/are covalently bonded to the molecule, and/or glycosylation sites which are present in the molecule are partially or completely deleted.

Furthermore, hIL-4 mutant proteins are particularly preferred in which amino acid 124 (tyrosine) is replaced with a naturally occurring amino acid and from 0 to one additional amino acid at positions 121 and/or 125 is replaced with another one of the possible amino acids, and in which, in addition, the N terminus and/or C terminus of the molecule is/are modified, and/or one or more polyethylene glycol molecules is/are covalently bonded to the molecule, and/or glycosylation sites which are present in the molecule are partially or completely deleted.

hIL-4 mutant proteins in which amino acid 124 (tyrosine) is replaced with aspartic acid or glutamic acid and position 121 is replaced with another of the possible amino acids, preferably aspartic acid or glutamic acid, and in which, in addition, the N terminus and/or C terminus of the molecule is modified, and/or one or more polyethylene glycol molecules is/are covalently bonded to the molecule, and/or glycosylation sites which are present in the molecule are partially or completely deleted, are particularly preferred from this group.

The insertion of an amino acid, preferably Ala, Gly, Pro, Ser. Thr or Val, particularly preferably Ala, between the N-terminal methionine and the natural N terminus of the hIL-4 mutant protein are preferred embodiments of the N-terminal modification in the abovementioned examples.

Examples of an expressed product of this type are:

Ala(−1)-Tyr(124)Asp (SEQ ID NO: 6)

Ala(−1)-Arg(121)Asp-Tyr(124)Asp (SEQ ID NO: 7)

Ala(−1)-Arg(121)Asp-Tyr(124)Asp-Ser(125)Asp (SEQ ID NO: 8)

Ala(−1)-Tyr(124)Asp-Ser(125)Asp (SEQ ID NO: 9)

Ala(−1)-Arg(121)Asp-Ser(125)Asp (SEQ ID NO: 10)

Preferred embodiments of the deletion of glycosylation sites in the abovementioned embodiments are the replacements of asparagine in position 38 with another naturally occurring amino acid, preferably aspartic acid, and/or asparagine in position 105 with another naturally occurring amino acid, preferably aspartic acid.

Examples of expressed products of this type are:

Asn(38)Asp-Asn(105)Asp-Tyr(124)Asp (SEQ ID NO: 11)

Asn(38)Asp-Asn(105)Asp-Arg(121)Asp-Tyr(124)Asp (SEQ ID NO: 12)

Asn(38)Asp-Asn(105)Asp-Arg(121)Asp-Tyr(124)Asp-Ser(125)Asp (SEQ ID NO: 13)

Asn(38)Asp-Asn(105)Asp-Tyr(124)Asp-Ser(125)Asp (SEQ ID NO: 14)

Asn(38)Asp-Asn(105)Asp-Arg(121)Asp-Ser(125)Asp (SEQ ID NO: 15)

hIL-4 can be produced as a recombinant protein (rhIL-4) by genetic manipulation, for example in *E. coli*. The protein which is formed in this context can be solubilized, renatured and isolated. The rhIL-4 then possesses a high specific biological activity which can be determined, for example, by measuring the DNA synthesis/proliferation of activated T cells or the CD23 expression of activated B cells [cf. Kruse, N. et al., (1991) FEBS Lett. 286, 58–60, Kikutani, H. et al., (1986) Cell 47, 657–665].

With regard to procuring a cDNA which encompasses a DNA region encoding the mature region of hIL-4, or which itself encodes the mature region of hIL-4, we refer to Yokota, T., Otsuka, T., Mosmann, T., Banchereau, J., DeFrance, T., Blanchard, D., De Vries, J. E., Lee, F. and Arai, K. I. (1986) Proc. Natl. Acad. Sci., USA 83, 5894–5898 and the literature cited in this reference. In the present context, "cDNA which encodes the mature region of hIL-4" is also understood as being cDNAs which, while possessing approximately the same number of base pairs, constitute mutants of the cDNA which is specified in a concrete manner in the state of the art, provided that the hIL-4 muteins which are thereby to be foreseen are likewise antagonists or partial agonists.

In the present context, Garr. C. et al., Biochemistry 1991, 30, 1515–1523 is followed with regard to numbering the DNA region encoding the mature region of hIL4.

cDNA which encodes the mature region of hIL4 can be isolated by excising an EcoRV/BamHI fragment from a recombinantly prepared cDNA (e.g. from British Bio-Technology Ltd., Oxford, England). The DNA fragment is integrated, with the addition of synthetic oligonucleotides, for example 5'-CATGCACAAGTGCGAT (SEQ ID NO: 1) and 5'-ATCGCACTTGTG (SEQ ID NO: 2), which contain the first 4 amino acid codons of interleukin 4 and also the codon for the start methionine, into an expression vector, for example between the NcoI and BamHI cleavage sites of the expression vector $pR^{TS}pRC$ 109 [cf. Weigel, U., Meyer, M. and Sebald, W. (1989) Eur. J. Biochem. 180, 295–300].

Amino acid sequence variants of IL4 are generated by introducing suitable altered nucleotides into the IL4-encoding DNA or by the in-vitro synthesis of the desired IL-4 form. Such variants include, for example, deletions or insertions or substitutions of residues within the IL-4 amino acid sequence. In this context, any combination of deletion, insertion and substitution is admissible for achieving the final construct, provided that the final construct exhibits the desired features. The amino acid changes can also alter the post-translational processing of IL-4: for example, the number or the positions of the glycosylation sites, the membrane-anchoring properties and/or the intracellular localization of IL-4 can be altered by insertion, deletion or some other influence on the leader sequence of the native IL-4.

When constructing amino acid sequence variants of IL-4, the location of the mutation site, and the nature of the mutation, depend on the property(ies) of IL-4 which is/are to be altered. The mutation sites can be altered individually or in series, for example by (1) substitution, initially with conservatively selected amino acids and then with more radical alternatives depending on the results achieved, (2) deletion of the target residue, or (3) insertion of residues in the vicinity of the localized site.

The "alanine-scanning mutagenesis" described by Cunningham and Wells (Science, 244: 1081–1085, 1989) is a suitable method for identifying particular IL-4 residues or regions as being preferred mutagenesis sites. In this case, a residue or a group of target residues is identified (e.g. charged residues such as Arg, Asp, His, Lys and Glu) and replaced by a neutral or negatively charged amino acid (most advantageously alanine or polyalanine) in order thereby to affect the interaction of the amino acids with the neighbouring aqueous environment inside or outside of the cell. The regions which react to the substitutions in a functionally sensitive manner are then worked up by introducing additional variants, or other variants, at the or for the substitution sites. This means that while the site for introducing an amino acid sequence alteration is predetermined, the nature of the alteration per se does not have to be predetermined.

In order, therefore, to optimize the performance of a mutation at a particular site, the method of Ala scanning or random mutagenesis can be carried out at the target codon or at the target region with the expressed IL-4 variants being tested for the optimum combination with regard to achieving the desired property.

Consequently, there are two main variables, i.e. the site of the mutation and the nature of the mutation, when constructing the amino acid sequence variants.

As a rule, the sizes of the deletions in an amino acid sequence are from about 1 to 30 residues, preferably from about 1 to 10 residues, and are sequential in the normal case. In the normal case, the deletions affect amino acid residues which are located immediately adjacent to each other.

The number of the successive deletions is selected such that the tertiary structure of IL-4, e.g. cysteine crosslinking, beta-pleated sheet structure or alpha helix, is retained in the affected region.

The insertions in an amino acid sequence include amino-terminal and/or carboxyl-terminal fusions having a length of from one single residue up to polypeptides having 100 or more residues and also insertions, which are located within a sequence, of individual or several amino acid residues. Insertions which are located within a sequence (i.e. insertions within the IL-4 sequence) can, inter alia, comprise from about 1 to 10 residues, preferably from 1 to 5 and, optimally, from 1 to 3 residues. Examples of terminal insertions are IL-4 having an N-terminal methionyl residue, an artefact of the direct expression of IL-4 in a recombinant bacterial cell culture, the insertion of one or more additional amino acids between methionine and the natural N terminus, for the purpose of facilitating elimination of the methionine, for example by bacterium-specific proteases, and the fusion of an heterologous N-terminal signal sequence to the N terminus of the IL-4 molecule, for the purpose of promoting the secretion of mature IL-4 from the recombinant host cells, and the fusion of polyamino acids, for example polyhistidine, for the purpose of facilitating the isolation of IL-4. As a rule, these signal sequences are selected from the host cell types which are foreseen and are therefore homologous with these types. Examples of suitable sequences are ompA, ompT, phoA, molE, amp or pelB, for *E. coli* cells, the alpha factor, amylase, invertase, killer toxin and mellitin prepro-peptide, for yeast cells, and viral signals, such as herpes gD, for mammalian cells.

A further preferred signal sequence is the natural signal sequence of interleukin 4.

Particular preference is given to those signal sequences which are eliminated by the expression organism itself so that the interleukin 4 mutant protein possesses the natural N terminus.

Expression products which are preferred following elimination of the signal sequence are:

Tyr(124)Asp (SEQ ID NO: 16)
Arg(121)Asp-Tyr(124)Asp (SEQ ID NO: 17)
Arg(121)Asp-Tyr(124)Asp-Ser(125)Asp (SEQ ID NO: 18)
Tyr(124)Asp-Ser(125)Asp (SEQ ID NO: 19)
Arg(121)Asp-Ser(125)Asp (SEQ ID NO: 20)

The other insertion variants of IL-4 include the fusion of immunogenic polypeptides, for example bacterial polypeptides such as beta-lactamase, or an enzyme encoded by the *E. coli* tip locus, or a yeast protein, to the N terminus or terminus of IL-4, and also C-terminal fusions with proteins having a long half life, such as immunoglobulin constant regions (or other immunoglobulin regions), albumin or ferritin—cf. description in WO 89/02922 (published on 6 Apr. 1989).

A further group of variants are those having an amino acid substitution. In these variants, at least one amino acid residue in the ILK4 molecule is replaced with another residue.

The naturally occurring residues are arranged into classes on the basis of side-chain characteristics which they possess in common:

1) hydrophobic: Met, Ala, Val, Leu and Ile;
2) neutral hydrophilic: Cys, Ser and Thr;
3) acidic: Asp and Glu;
4) basic: Asn, Gln, His, Lys and Arg;
5) residues having an effect on chain orientation: Gly and Pro; and
6) aromatic: Trp, Tyr and Phe.

Non-conservative substitutions involve replacing a representative of one of these classes with that of another.

Amino acid substitutions are used, inter alia, when altering the native glycosylation pattern of the polypeptide. "Altering" means deleting one or more of the carbohydrate skeletons in the native IL-4 and/or adding one or more glycosylation sites which are not present in the native IL-4.

Normally, the glycosylation of the polypeptides is either N-linked or O-linked. "N-linked" refers to coupling of the carbohydrate skeleton to the side chain of an asparagine residue. The tri-peptide sequences asparagine-X-serine and asparagine-X-threonine, where X can be any amino acid with the exception of proline, are the recognition sequences for the enzymic coupling of the carbohydrate skeleton to the asparagine side chain. Consequently, the presence of one of these tri-peptide sequences in a polypeptide creates a potential glycosylation site.

"O-linked" refers to the coupling of one of the sugars N-acetylgalactosamine, galactose or xylose to an hydroxyamino acid, inter alia serine or threonine, although 4-hydroxyproline or 5-hydroxylysine can also be used.

The addition of glycosylation sites to IL-4 is effected without difficulty by altering the amino acid sequence in such a way that this sequence contains one or more of the above-described tri-peptide sequences (for N-linked glycosylation sites). The alteration can likewise be effected by adding or substituting one or more serine or threonine residues to the native IL-4 sequence (for O-linked glycosylation sites). With a view to simplifying the procedure, the IL-4 amino acid sequence is preferably changed by means of carrying out alterations at the DNA level, in particular by mutating the IL-4-encoding DNA at previously selected bases such that codons are produced which are translated into the desired amino acids. In an analogous manner, one or more of the tri-peptide sequences which are present (for N-linked glycosylation) are modified by substituting or deleting the whole or parts of the tri-peptide when deletion of the carbohydrate skeleton is desired. In the case of O-glycosylation sites, the carbohydrate skeleton can be deleted by substituting or deleting the corresponding amino acid.

The chemical or enzymic coupling of glycosides to the polypeptide represents a further option for increasing the number of carbohydrate skeletons in IL-4. These methods are advantageous insofar as they do not require the polypeptide to be prepared in a host cell which is able to carry out N-linked and O-linked glycosylation. Depending on the coupling mechanism used, the sugar(s) can be linked to (a) arginine and histidine, (b) free carboxyl groups, (c) free sulphydryl groups, such as those of cysteine, (d) free hydroxyl groups, such as those of serine, threonine or hydroxyproline, (e) aromatic residues, such as those of phenylalanine, tyrosine or tryptophan, or (f) the amido group of glutamine. These methods are described in WO 87/05330, which was published on 11 Sep. 1987, and in Aplin and Wriston (CRC Crit. Rev. Biochem., pp. 259–306 [1981]).

In addition to the abovementioned method, chemical or enzymic means can also be used for removing the carbohydrate skeletons which are present in the native IL-4. In the case of chemical deglycosylation, it is necessary to expose the polypeptide to the compound trifluoromethanesulphonic acid or an equivalent compound. While this treatment results in most or all of the sugars being eliminated apart from the linking sugar (N-acetylglucosamine or N-acetylgalactosamine), it leaves the polypeptide intact. Chemical deglycosylation is described by Hakkimuddin et al., Arch. Biochem. Biophys., 259:52 (1987) and by Edge et al., Anal. Biochem., 118:131 (1981). Carbohydrate skeletons in the polypeptides can be eliminated enzymically using a series of endoglycosidases and exoglycosidases, as described by Thotakura et al., (Meth. Enzymol., 138:350 [1987]).

Glycosylation at the potential glycosylation sites can be prevented by using the compound tunicamycin, as described by Duskin et al. (J. Biol. Chem., 257:3105 [1982]). Tunicamycin blocks the formation of protein-N-glycoside linkages.

A further type of covalent modification of IL-4 includes linking IL-4 to different non-protein polymers, for example polyethylene glycol, polypropylene glycol or polyoxyalkylenes, as described in U.S. Pat. Nos. 4,640,835; 4,496,689; 4,301,144; 4,670,417; 4,791,192 or 4,179,337.

The agent used for the crosslinking, the degree of substitution and the reaction conditions are selected by means of experiments using bifunctional agents preferably using a series of reagents each of which reacts with a different side chain.

One option, which is preferably used, for improving the half life of a protein which is circulating in vivo is that of conjugating it to a polymer, which confers a longer half life on it. Thus, for example, the conjugation of polyethylene glycol (PEG) to Cl-NH has proved to be an excellent way of increasing the half life. PEG is a non-immunogenic, linear, uncharged polymer possessing three water molecules per molecule of ethylene oxide, so that the hydrodynamic properties of the conjugated molecules can be altered dramatically (Maxfield et al., Polymer, 16:505–509 (1975); Bailey, F. E., et al., in: Nonionic surfactants [Schick, M. J., Ed.] pp. 794–821, 1967). Several enzymes which are used therapeutically have been linked to PEG with the aim of effectively increasing their in-vivo half life (Abuchowski, A. et al., J. Biol. Chem. 252:3582–3586, 1977; Abuchowski, A. et al., Cancer Biochem. Biophys., 7:175–186, 1984). It is reported that linking IL-2 (interleukin 2) to PEG not only extends its survival time in the circulation but also increases its potency (Katre, N. V. et al., Proc. Natl. Acad. Sci., 84:1487–1491 (1987); Goodson, R. et al., Bio/Technology, 8:343–346, 1990). Linking PEG to other molecules has been reported to decrease their immnunogenicity and toxicity (Abuchowski, A. et al., J. Biol. Chem. 252:3578–3581, 1977).

IL-4 can also be included in microcapsules, which are prepared, for example, by coacervation techniques or by "interfacial polymerization" (e.g. hydroxymethylcellulose or gelatine microcapsules and poly-[methyl methacrylate] microcapsules), in colloidal drug-release systems (e.g. liposomes, albumin microspheres, microemulsions, nanoparticles and nanocapsules) or in macroemulsions. Such techniques are mentioned in Remington's Pharmaceutical Sciences, 16th edition, Osol, A., Ed. (1980).

IL-4 preparations are also suitable for use in isolating antibodies, as standards for IL-4 assays (e.g. by labelling IL-4 for its use as a standard in a radio immunoassay, an enzyme-coupled immunoassay or in a radio receptor assay), in affinity purification techniques and in receptor binding assays (of the competitive type) when labelled with radioiodide, enzymes, fluorophores, spin labels, etc.

Since it is difficult to predict the properties of an IL-4 variant, it will be understood that a certain screening of the resultant variant is required in order to achieve the optimum variant. Thus, for example, a change in the immunological character of the IL-4 molecule, for example its affinity for a particular antibody, is measured by a competitive immunoassay. The variant is examined for changes involving the diminution or amplification of its activity as compared with the activity of the native IL-4 which is observed in the same assay. Other potential changes in the protein or polypeptide properties, for example redox, or thermal stability, hydrophobicity, sensitivity towards proteolytic degradation, stability in the recombinant cell culture or in plasma, or else the tendency to aggregate with carriers or to form multimers, are determined by methods which are state of the art.

Therapeutic Formulations and Administration of IL-4

The novel compounds either inhibit interleukin 4-mediated processes or compete with hIL-4. They are therefore suitable for treating overshooting or falsely regulated immune reactions and autoimmune diseases. These also include immune deficiencies of both primary and secondary nature. In addition to this, the antagonist can be employed both in transplantations and in the palliative therapy of tumour diseases. These include, for example:

allergies (blocking of the primary response and the IgE-mediated response; desensitizing in the case of known allergies; atopic diseases; alleviation in association with asthma attacks; hyper IgE syndrome).

Transplantations (reduction in HLA-DR expression in organ transplantation, suppression of the GVHR, use when purging bone marrow)

Leukaemias and solid tumours expressing IL-4 receptor (reduction of an overshooting autocrine IL-4 production; inhibition of tumour growth)

Counter-regulation in association with the overproduction of thrombocytes

Therapy of coagulation disturbances (via monocyte block)

Use in disturbances of lipid metabolism

Correction in disturbances of carbohydrate balance

Improvement of the immune status in infections (sepsis).

Due to its good solubility in water, the IL-4 mutant protein can be employed both systemically and locally, i.e. topically, inter alia as an inhalation spray. It is also possible for it to be formulated as a slow-release preparation. A short-term therapy or a continuous therapy is possible in the case of all the therapy forms.

Therapeutic formulations of the IL-4 antagonist are prepared for storage by mixing the IL-4 antagonist, after achieving the desired degree of purity, with physiologically acceptable carriers, auxiliary substances or stabilizers (Remington's Pharmaceutical Sciences, loc. cit.) in the form of a lyophilisate or of aqueous solutions. Acceptable carriers, auxiliary substances or stabilizers are not toxic for the recipient at the dosages and concentrations employed; they include buffers such as phosphate, citrate and other organic acids; antioxidants such as ascorbic acid; low molecular weight polypeptides (less than approximately 10 residues), proteins such as serum albumin, gelatin or immunoglobulins; hydrophilic polymers such as polyvinylpyrrolidone; amino acids such as glycine, glutamine, asparagine, arginine or lysine; monosaccharides, disaccharides and other carbohydrates, for example glucose, mannose or dextrin; chelating agents such as EDTA; sugar alcohols such as mannitol or sorbitol; salt-forming counter-ions such as sodium and/or non-ionic surface-active substances such as Tween, Pluronics or polyethylene glycol (PEG).

For in-vivo use, an IL-4 antagonist must be sterile. This is readily achieved by filtration through sterile membrane filters, either before or after lyophilization and reconstitution. The IL-4 antagonist is normally stored in lyophilized form or in solution.

Suitable examples of preparations having a delayed release are, for example, semipermeable matrices consisting of solid hydrophobic polymers which contain the protein; these matrices are shaped articles, for example film tablets or microcapsules. Examples of matrices having a delayed release are polyesters, hydrogels [e.g. poly(2-hydroxyethyl methacrylate)—described by Langer et al., J. Biomed. Mater. Res., 15:167–277 [1981] and Langer, Chem. Tech., 12:98–105 [1982]—or poly(vinyl alcohol)], polyactides (U.S. Pat. No. 3,773,919, EP 58,481), copolymers of L-glutamic acid and gamma-ethyl-L-glutamate (Sidman et al., Biopolymers, 22:547–556 [1983]), non-degradable ethylene/vinyl acetate (Langer et al., loc. sit.), degradable lactic acid/glycolic acid copolymers such as Lupron DepotTM (injectable microspheres consisting of lactic acid/ glycolic acid copolymer and leuprolide acetate) and poly-D-(-)-3-hydroxybutyric acid (EP 133,988). While polymers such as ethylene/vinyl acetate and lactic acid/glycolic acid enable the molecules to be released for periods of greater than 100 days, the proteins are released over relatively short periods of time in the case of some hydrogels. If encapsulated proteins remain in the body over relatively long periods of time, they can then be denatured or aggregated by moisture at 37° C., resulting in a loss of biological activity and possible changes in immunogenicity. Meaningful strategies for stabilizing the proteins can be developed, depending on the mechanism involved. If it is found, for example, that the mechanism which leads to the aggregation is based on intermolecular S-S bridge formation as a result of thiodisulphide exchange, stabilization can be achieved by modifying the sulphydryl radicals, lyophilizing from acid solutions, controlling the moisture content, using suitable additives and developing special polymer/matrix compositions.

The formulations of an IL-4 antagonist exhibiting delayed release also include IL-4 antagonists which are enclosed in liposomes. IL-4 antagonist-containing liposomes are prepared by methods which are known per se: DE 3,218,121; Epstein et al., Proc. Natl. Acad. Sci. USA, 82;3688–3692 (1985); Hwang et al., Proc. Natl. Acad. Sci. USA, 77:4030–4034 (1980); EP 52,322; EP 36,676; EP 88,046; EP 143,949; EP 142,641; Japanese Patent Application 83-118008; U.S. Pat. Nos. 4,485,045 and 4,544,545; and also EP 102,324. As a rule, the liposomes are of the small (approximately 200–800 Angstrom) unilamellar type having a lipid content of greater than approximately 30 mol % cholesterol, with the proportion in each case being adjusted for the optimum IL-4 antagonists. Liposomes exhibiting an extended circulation time are disclosed in U.S. Pat. No. 5,013,556.

A further application of the invention relates to the incorporation of IL-4 antagonists into "shaped articles". These latter may be employed for modulating or preventing the occurrence of a shock.

EXAMPLE 1

Removal of potential N-glycosylation sites in hIL4 mutant proteins

Two asparagine-coupled glycosylation sites are present at amino acid positions 38 and 105 in the natural hIL-4 amino acid sequence. The corresponding codons in the structural gene can be replaced with those for aspartic acid. This prevents N-glycosylation of the resulting hIL-4 mutant protein when its gene is expressed in yeast strains.

The two codon replacements (site-directed mutagenesis) in the structural gene for hIL-4 mutant proteins were carried out in accordance with the method of Deng and Nickoloff [Anal. Biochem. 200:81 (1992)] using the cloning vector pUC18. The synthetic oligonucleotides which were required for altering the structural gene had the following sequences:

a) for replacing asparagine with aspartic acid in position 38:

5'-GCC TCC AAG GAC ACA ACT GAG-3' (SEQ ID NO: 3)

b) for replacing asparagine with aspartic acid in position 105:

5'-GTG AAG GAA GCC GAC CAG AGT ACG-3'(SEQ ID NO: 4).

The positions which are underlined in the given nucleotide sequences indicate the codons for aspartic acid.

The codon replacement in the nucleotide sequence was confirmed by DNA sequencing. The altered structural gene was inserted into yeast expression vectors and expressed in suitable strains.

EXAMPLE 2

Insertion of an amino acid in position (+2) for the purpose of preparing, in E. coli, an IL mutein without an N-terminal methionine In order to prepare an IL-4 mutein which lacks the N-terminal methionine, an amino acid was inserted, in position (+2), which leads to the elimination of the N-terminal methionine, in E. coli, by means of a specific methionine aminopeptidase (Flinta et al., Eur. J. Biochem. 15, 193–196, 1986). For this, the vector RPR9-IL4-Y 124D (enclosure 1) was cut with the restriction endonucleases XhoI and BamHI. The resulting DNA fragment of approx. 450 bp in length, which carries the sequence information for the IL4Y124D gene and a short (approx. 50 bp) fragment from the atpE region of the vector, was purified by agarose gel electrophoresis and recloned into the vector M13mp18, which had been cut with SalI and BamHI. Single-stranded DNA was prepared and subjected to an in-vitro mutagenesis reaction using the following oligonucleotide:

5' CTGGAGACTGCCATGGCCCACAAGTGC-GATATCACC3' (SEQ ID NO: 5).

As a result of this mutagenesis, the amino acid alanine (codon GCC) is introduced in position (+2) of the IL4Y124D gene. In addition, an NcoI cleavage site (CCATGG) is inserted at the 5' end of the gene in order to facilitate the subsequent screening and cloning into an expression vector. The plaques were screened by means of a restriction analysis using double-stranded M13 RF DNA (replicative form). Positive clones were identified by restriction digestion with the enzymes NcoI and BamHI. In addition, the correct sequence was confirmed by sequencing.

A DNA fragment of approx. 400 bp in length was excised with NcoI and BamHI from a selected M13mp18 clone, purified by means of agarose gel electrophoresis and cloned into the vector pTrc99A (commercially available from Pharmacia P-L Biochemicals), which had likewise been cut with NcoI and BamHI. E. coli cells (TGl) were transformed with the vector, pAPH100 (IL4Y125D), which resulted from this cloning and selected on ampicillin-containing nutrient medium. Expression of the protein, and its purification, resulted in an IL-4 mutein which lacked the N-terminal methionine.

EXAMPLE 3

Fermentation of the yeast cells

Nutrient solutions:

The following nutrient solutions were used for culturing the yeast cells expressing hIL4 mutant proteins:

| Ingredient | Nutrient solution SD2 | Sc6 |
| --- | --- | --- |
| Bacto yeast nitrogen base | 6.7 g/l | — |
| Difco yeast extract | — | 20.0 g/l |
| Glucose | 20.0 g/l | 5.0 g/l |
| KH$_2$PO$_4$ | 6.7 g/l | 1.4 g/l |
| (NH$_4$)$_2$SO$_4$ | — | 2.0 g/l |
| MgSO$_4$ × 7 H$_2$O | — | 0.5 g/l |
| Antifoam PPG 2000 | — | 0.1 g/l |

The ingredients were mixed in demineralized water and the pH was adjusted to 5.5. The mixture was sterilized at 121° C. for 20 min. Glucose was dissolved in ⅕ of the requisite volume of demineralized water, with this solution being sterilized separately and then added to the remaining nutrient solution after cooling.

Strain stocks:

Strain stocks of all the yeast transformants were laid down by talking 2 ml aliquots of a preliminary culture and storing them in liquid nitrogen.

Preliminary cultures:

The preliminary culture fermentations were carried out in 1 ltr. shaking flasks which contained 200 ml of SD2 nutrient solution. The nutrient solution was inoculated with a strain stock or with a single colony from an SD2 agar plate. The cultures were incubated at 26–30° C. for 2–3 days while being shaken continuously.

Main culture fermentations:

The main culture fermentations were carried out in Sc6 nutrient solution using 10 ltr. stirred tank fermenters. The nutrient solution was inoculated with 3–5% by vol. of a preliminary culture, with the biomass being centrifuged out of the preliminary culture and resuspended in Sc6 medium prior to the inoculation. The fermentation conditions for the 10 ltr. main culture were as follows:

| | |
| --- | --- |
| Temperature | 26–30° C. |
| Stirrer revolution rate | 600 rpm |
| Aeration rate | 0.5 vvm |
| pH set point | 5.5 (correction with 5 N NaOH and 5 N H$_2$SO$_4$) |

From a fermentation time of 5 hrs. onwards, the cultures were fed continuously with glucose and yeast extract. The feeding rate was regulated on the basis of the respiratory quotient (RQ value) of the culture. The RQ set point was 1.0. The feed solution had the following composition:

Glucose 500 g/l

Difco yeast extract 75 g/l

The constituents were dissolved separately in demineralized water and the solutions were sterilized at 121° C. for 20 min. The two solutions were combined after having been cooled.

When the induced Gal10 promoter, or a derivative of the Gal10 promoter, was used, induction was effected by changing the carbohydrate in the feed solution from glucose (500 g/l) to galactose (500 g/l). After that, the feeding rate was no longer controlled on the basis of the RQ value. The feeding rate was adjusted manually to double the value of the feeding rate at the time of induction. The Gal10 promoter was normally induced after a fermentation period of about 48 hrs.

Cell harvesting:

After the fermentation had finished (80–120 hrs.), the contents of the fermenter were cooled down to 10–15° C. and, in the case of intracellular expression, the yeast cells were harvested using standard centrifugation techniques (e.g. bucket centrifuge). The cell mass which was obtained after centrifugation was cryopelleted, by adding it directly dropwise to liquid nitrogen, and stored at −80° C. The product was worked up from the biomass which had been treated in this way. When the heterologous protein was secreted into the culture broth, the yeast cells were then separated from the culture broth using standard centrifugation techniques (e.g. bucket centrifuge) or by means of crosscurrent microfiltration (e.g. Filtron-Minisette system). If necessary, the culture broth was sterilized by filtration. The product was subsequently worked up from the cell-free culture broth.

EXAMPLE 4

Fermentation of *E. coli*

Nutrient solutions:

The *E. coli* transformants expressing hIL4 mutant proteins were cultured in LB nutrient solution of the following composition:

Bacto tryptone 10 g/l

Bacto yeast extract 5 g/l

NaCl 10 g/l

The constituents were dissolved in deionized water and this solution was sterilized at 121° C. for 20 min. Prior to inoculation, an antibiotic which was suitable for selecting the transformants (e.g. 100 mg/l Na ampicillin or 50 mg/l kanamycin sulphate depending on the selection marker used in the vector) was added to the nutrient solution under sterile conditions.

Strain stocks:

Strain stocks of all the *E. coli* transformants were laid down by taking 2 ml aliquots of a preliminary culture and storing them in liquid nitrogen.

Preliminary cultures:

The preliminary culture fermentations were carried out in 1 ltr. shaking flasks which contained 200 ml of LB nutrient solution. The nutrient solution was inoculated with a strain stock or with a single colony from an LB agar plate. The cultures were incubated at 30° C. for 12–18 hrs. while being shaken continuously.

Main culture fermentations:

The main culture fermentations were carried out in LB nutrient solution using 10 ltr. stirred tank fermenters. The nutrient solution was inoculated with 1–5% by vol. of a preliminary culture, with the biomass being centrifuged out of the preliminary culture and resuspended in fresh LB medium prior to the inoculation. The fermentation conditions for the 10 ltr. main culture were as follows:

| | |
|---|---|
| Starting temperature | 30° C. (when using temperature-inducible promoters) |
| | 37° C. (when using IPTG-inducible vectors) |
| Stirrer revolution rate | 500 rpm |
| Aeration rate | 0.5 vvm |

In order to monitor the growth of the biomass, sterile samples were removed from the culture broth at intervals of approx. 1 hr. and their optical density was determined at 600 nm (OD600). The cultures were induced when an OD600 of 0.8–1.2 had been reached. Induction took place as follows, depending on the promoter which had been selected:

| | |
|---|---|
| Temperature induction: | Increase of the fermentation temperature from 30° C. to 42° C. |
| IPTG induction: | Sterile addition of isopropyl-β-D-thio-galactopyranoside (IPTG) to a concentration of 0.4 mM |

The induction time was typically 4–8 hrs.

Cell harvesting:

After the fermentation had finished (6–14 hrs.), the contents of the fermenter were cooled down to 10–15° C. and the bacterial cells were harvested using standard centrifugation techniques (e.g. bucket centrifuge). The cell mass which was obtained after centrifugation was temporarily stored, where appropriate, in the frozen state. The product was worked up from the biomass which had been obtained in this way.

EXAMPLE 5

Expression of interleukin 4 mutant proteins in yeast cells using, constitutive promoters Yeast transformants which harboured an expression vector containing a gene encoding an hIL-4 mutant protein and a constitutive promoter (e.g. alpha mating factor promoter, GAPDH promoter or TPI promoter) were cultured at 28° C. on a 10 ltr. scale. During the fermentation, SDS-PAGE was used for testing qualitatively for expression of the hIL-4 mutant protein. The total fermentation time was 96 hrs. The biomass concentration achieved at the end of the fermentation was 27 g of dry weight/l. After the cells had been separated off by centrifugation (15 min, 6,500× g, 4° C.), and after sterilization by filtration, the product was worked up from the cell-free culture broth.

EXAMPLE 6

Expression of interleukin 4 mutant proteins in yeast cells using inducible promoters Yeast transformants which harboured an expression vector containing a gene encoding an hIL-4 mutant protein and an inducible promoter (e.g. Gal10 promoter or a derivative of a Gal10 promoter) were cultured at 28° C. on a 10 ltr. scale. After a fermentation period of 48 hrs., induction was effected by changing the carbohydrate used in the feed solution from glucose to galactose. During the fermentation, SDS-PAGE was used for testing qualitatively for expression of the hIL-4 mutant protein. The total fermentation time was 96 hrs. The biomass concentration which was achieved at the end of the fermentation was 24 g of dry weight/l. After the cells had been separated off, and after sterilization by filtration, the product was worked up from the cell-free culture broth.

Other inducible promoters can also be employed, in analogy with this process, for expressing hIL-4 mutant proteins. A suitable induction technique has to be employed which depends on the nature of the promoter which is chosen.

EXAMPLE 7

Expression of interleukin 4 mutant proteins in E. coli using inducible promoters E. coli transformants which harboured an expression vector containing a gene encoding an hIL-4 mutant protein and a temperature-inducible promoter (e.g. λpL promoter or a derivative of the λpL promoter) were cultured in LB nutrient solution on a 10 ltr. scale. The vector-containing cells were selected by adding 100 mg/l Na ampicillin to the LB nutrient solution (=LB+Amp nutrient solution). The main culture batches were inoculated with 5% by vol. of a 14 hr-old preliminary culture in LB+Amp nutrient solution. At the beginning of the fermentation, the fermentation temperature was 30° C. and was raised to 42° C. after an OD600 of 0.8–1.2 had been reached in order to induce the temperature-sensitive promoter. During the fermentation, SDS-PAGE was used for testing qualitatively for expression of the hIL-4 mutant protein. After an induction period of 4–6 hrs., the fermentation was terminated by cooling the culture broth down to 10–15° C. The biomass concentration which was achieved at the end of the fermentation was approx. 5 g of fresh weight/l. The E. coli cells were harvested by centrifugation in a bucket centrifuge (15 min., 6,500× g, 4° C.) and the cell mass was cryopelleted by directly adding it dropwise to liquid nitrogen. The biomass which had been deep-frozen in this way was then stored at −80° C. The product was worked up from the biomass which had been treated in this way.

Other inducible promoters may also be employed, in analogy with this process, for expressing hIL-4 mutant proteins in E. coli. A suitable induction technique has to be used which depends on the nature of the promoter which is chosen.

EXAMPLE 8

Working up of an IL-4 mutant protein

Cell disruption and isolation of the inclusion bodies 25 g of E. coli moist mass from Example 7 were taken up in 200 ml of buffer (0.1 M phosphate buffer, pH 7.3, 0.1% Triton, 1 mM EDTA, 1 μg/ml pepstatin) and disrupted by sonication (Branson B 15 sonifier). The inclusion bodies, which contain the product, were isolated by centrifugation (35,000× g, 20 min) and washed in disruption buffer which additionally contained 4 M urea.

Solubilization and sulphitolysis of the product

The washed inclusion bodies were solubilized in 125 ml of buffer (0.2 M Tris, pH 8.1, 8 M guanidine hydrochloride). 4 g of sodium sulphite and 2 g of potassium tetrathionate were added and the reaction mixture was stirred for 2 h. Undissolved constituents were removed by centrifugation (35,000× g, 20 min) after the reaction had finished.

Gel filtration

The supernatant was loaded on to a gel filtration column (Sephacryl S-300 HR, Pharmacia, 10×90 cm) and subjected to gel filtration in PBS buffer containing 6 M guanidine hydrochloride at a flow rate of 280 ml/h. Product-containing fractions were identified by means of SDS-PAGE and combined.

Renaturation

β-Mercaptoethanol (final concentration 15 mM) was added in order to reduce the molecules. Following a two-hour incubation at room temperature, the mixture was diluted 5 times with water and dialyzed against buffer (3 mM $NaH_2PO_4$, 7 mM $Na_2HPO_4$, 2 mM KCl, 120 mM NaCl) for 3–4 days.

Concentration

The dialyzed material was adjust ed to pH 5 with acetic acid and its conductivity was decreased to $\leq 10$ mS/cm by adding water. 50 ml of CM Sepharose-FF (Pharmacia), which was equilibrated with 25 mM ammonium acetate, pH 5.0, were added to the mixture while stirring. Unbound material was filtered off and the gel was used to fill a column. The product was eluted with a linear gradient of from 0 to 1 M NaCl in 25 mM ammonium acetate, pH 5.0, at a flow rate of 300 ml/h. Product-containing fractions were identified by SDS-PAGE or by analytical RP chromatography.

Final purification

The pool of CM sepharose was loaded on to a Vydac C-4 column (1×25 cm, 10 μm) which was equilibrated with 0.1% TFA and eluted with an increasing gradient of acetonitrile. Fractions which contained the pure product were combined and lyophilized.

What is claimed is:

1. A mutant human interleukin-4 (hIL-4) protein consisting of the amino acid sequence of wild-type hIL-4 with two modifications, wherein the first modification is selected from the group consisting of the replacement of one or more of the amino acids occurring in the wild-type hIL-4 protein at positions 121, 124 or 125 with another natural amino acid, and the second modification is at least one modification selected from the group consisting of:
   a) the modification of the N-terminus therein;
   b) the modification of the C-terminus therein;
   c) the deletion of potential glycosylation sites therein; and/or
   d) the coupling of the protein to a non-protein polymer;
said mutant hIL-4 protein being an antagonist or partial agonist of wild-type hIL-4.

2. A mutant hIL-4 protein according to claim 1, which consists of the amino acid sequence of wild-type hIL-4 with two modifications, wherein the first modification is selected from the group consisting of the replacement of one or more of the amino acids occurring in the wild-type hIL-4 protein at positions 121, 124 or 125 by another natural amino acid, and the second modification is at least one modification selected from the group consisting of:
   a) the modification of the N-terminus therein by the deletion or insertion of one or more amino acids;
   b) the modification of the C-terminus therein by the deletion or insertion of one or more amino acids;
   c) the deletion of potential glycosylation sites; and/or
   d) the coupling of the protein to a non-protein polymer selected from the group consisting of polyethylene glycol, polypropylene glycol and polyoxyalkylenes;
said mutant hIL-4 protein being an antagonist or partial agonist of wild-type hIL-4.

3. A mutant hIL-4 protein according to claim 2, which consists of the amino acid sequence of wild-type hIL-4 with two modifications, wherein the first modification is selected from the group consisting of the replacement of one or more of the amino acids occurring in the wild-type hIL-4 protein at positions 121, 124 or 125 is replaced by another natural amino acid, and the second modification comprises the modification of the N-terminus therein by the insertion before the natural N-terminal histidine residue of an amino acid selected from the group consisting of alanine, glycine, proline, serine, threonine and valine, said mutant hIL-4 protein being an antagonist or partial agonist of wild-type hIL-4.

4. A mutant hIL-4 protein according to claim 3, wherein said second modification further comprises:
   a) the deletion of the potential glycosylation sites at positions 38 and/or 105 by replacement of asparagine in these positions by aspartic acid; and/or
   b) the coupling of the protein to polyethylene glycol.

5. A therapeutic composition comprising:
   a) a mutant human interleukin-4 (hIL-4) protein according to claim 3; and
   b) a physiologically acceptable carrier.

6. A therapeutic composition comprising:
   a) a mutant human interleukin-4 (hIL-4) protein according to claim 2; and
   b) a physiologically acceptable carrier.

7. A therapeutic composition comprising:
   a) a mutant human interleukin-4 (hIL-4) protein according to claim 3; and
   b) a physiologically acceptable carrier.

8. A therapeutic composition comprising:
   a) a mutant human interleukin-4 (hIL-4) protein according to claim 4; and
   b) a physiologically acceptable carrier.

9. A method of antagonizing or partially agonizing the effect of human interleukin-4 (hIL-4) comprising contacting cells expressing the hIL-4-receptor with an antagonistic or partially agonistic effective amount of a mutant hIL-4 protein according to claim 1.

10. A method of antagonizing or partially agonizing the effect of human interleukin-4 (hIL-4) comprising contacting cells expressing the hIL-4-receptor with an antagonistic or partially agonistic effective amount of a mutant hIL-4 protein according to claim 2.

11. A method of antagonizing or partially agonizing the effect of human interleukin-4 (hIL-4) comprising contacting cells expressing the hIL-4-receptor with an antagonistic or partially agonistic effective amount of a mutant hIL-4 protein according to claim 3.

12. A method of antagonizing or partially agonizing the effect of human interleukin-4 (hIL-4) comprising contacting cells expressing the hIL-4-receptor with an antagonistic or partially agonistic effective amount of a mutant hIL-4 protein according to claim 4.

* * * * *

(12) EX PARTE REEXAMINATION CERTIFICATE (6436th)
United States Patent
Wild et al.

(10) Number: US 6,130,318 C1
(45) Certificate Issued: *Sep. 16, 2008

(54) HIL-4 MUTANT PROTEINS USED AS ANTAGONISTS OR PARTIAL AGONISTS OF HUMAN INTERLEUKIN 4

(75) Inventors: Hanno Wild, Wuppertal (DE); Rudolf Hanko, Düsseldorf (DE); Michael Dörschug, Heiligenhaus (DE); Hans-Dietrich Hörlein, Wuppertal (DE); Jürgen Beunink, Wuppertal (DE); Heiner Apeler, Wuppertal (DE); Hermann Wehlmann, Wuppertal (DE); Walter Sebald, Würzburg (DE)

(73) Assignee: Bayer Aktiengesellschaft, Leverkusen (DE)

Reexamination Request:
No. 90/008,716, Jun. 21, 2007

Reexamination Certificate for:
Patent No.: 6,130,318
Issued: Oct. 10, 2000
Appl. No.: 08/765,012
Filed: Dec. 19, 1996

( * ) Notice: This patent is subject to a terminal disclaimer.

(22) PCT Filed: Dec. 19, 1996

(86) PCT No.: PCT/EP95/02358
§ 371 (c)(1),
(2), (4) Date: Dec. 19, 1996

(87) PCT Pub. No.: WO96/01274
PCT Pub. Date: Jan. 18, 1996

(51) Int. Cl.
*A61K 38/00* (2006.01)
*A61K 38/20* (2006.01)
*C07K 14/54* (2006.01)
*C07K 14/435* (2006.01)

(52) U.S. Cl. .................. 530/351; 424/85.1; 424/85.2
(58) Field of Classification Search .................. None
See application file for complete search history.

(56) References Cited

U.S. PATENT DOCUMENTS

| | | | | |
|---|---|---|---|---|
| 5,359,030 A | * | 10/1994 | Ekwuribe | 530/303 |
| 5,723,118 A | * | 3/1998 | Sebald | 424/85.2 |
| 5,986,059 A | | 11/1999 | Shanafelt et al. | |
| 6,028,176 A | | 2/2000 | Greve et al. | |
| 6,313,272 B1 | | 11/2001 | Greve et al. | |
| 6,335,426 B1 | | 1/2002 | Shanafelt et al. | |
| 2005/0059590 A1 | | 3/2005 | Pan et al. | |

FOREIGN PATENT DOCUMENTS

WO WO 8804667 A1 * 6/1988

OTHER PUBLICATIONS

Katre et al. PNAS USA vol. 84 (Mar. 1987) pp. 1487–1491.*
Hans–Peter Tony et al., "Design of human interleukin–4 antagonists inhibiting interleukin–4–dependent and interleukin–13–dependent responses in T–cells and B–cells with high efficiency", Eur. J. Biochem. 225, 659–665 (1994).

* cited by examiner

*Primary Examiner*—Bennett Celsa

(57) ABSTRACT

The present invention relates to novel hIL-4 mutant proteins, to processes for preparing them, and to their use as medicaments, in particular in overshooting, falsely regulated immune reactions and autoimmune diseases.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–2, 9, 10 and 11 are determined to be patentable as amended.

Claim 6, dependent on an amended claim, is determined to be patentable.

New claims 13–17 are added and determined to be patentable.

Claims 3–5, 7–8 and 12 were not reexamined.

1. A mutant human interleukin-4 (hIL-4) protein consisting of the amino acid sequence of wild-type hIL-4 with two modifications, wherein the first modification is [selected from the group consisting of] the replacement of [one or more of] the amino acids occurring in the wild-type hIL-4 protein at positions 121[,] *and* 124 [or 125] with [another natural amino] *aspartic* acid, and the second modification is at least one modification selected from the group consisting of:
   a) the modification of the N-terminus therein;
   b) the modification of the C-terminus therein;
   c) the deletion of potential glycosylation sites therein; and/or
   d) the coupling of the protein to a non-protein polymer;
said mutant hIL-4 protein being an antagonist [or partial agonist] of wild-type hIL-4.

2. A mutant hIL-4 protein according to claim 1, [which consists of the amino acid sequence of wild type hIL-4 with two modifications,] wherein [the first modification is selected from the group consisting of the replacement of one or more of the amino acids occurring in the wild type hIL-4 protein at positions 121, 124 or 125 by another natural amino acid, and] the second modification is at least one modification selected from the group consisting of:
   a) the modification of the N-terminus therein by the deletion or insertion of one or more amino acids;
   b) the modification of the C-terminus therein by the deletion or insertion of one or more amino acids;
   c) the deletion of potential glycosylation sites; and/or
   d) the coupling of the protein to a non-protein polymer selected from the group consisting of polyethylene glycol, polypropylene glycol and polyoxyalkylenes;
said mutant hIL-4 protein being an antagonist [or partial agonist] of wild-type hIL-4.

9. A method of antagonizing [or partially agonizing] the effect of human interleukin-4 (hIL-4) comprising contacting cells expressing the hIL-4-receptor with an antagonistic [or partially agonistic] effective amount of a mutant hIL-4 protein according to claim 1.

10. A method of antagonizing [or partially agonizing] the effect of human interleukin-4 (hIL-4) comprising contacting cells expressing the hIL-4-receptor with an antagonistic [or partially agonistic] effective amount of a mutant hIL-4 protein according to claim 2.

11. A method of antagonizing [or partially agonizing] the effect of human interleukin-4 (hIL-4) comprising contacting cells expressing the hIL-4-receptor with an antagonistic [or partially agonistic] effective amount of a mutant hIL-4 protein according to claim 3.

*13. A mutant hIL-4 protein according to claim 1 wherein the second modification comprises an N-terminal methionyl residue.*

*14. A mutant hIL-4 protein according to claim 1 wherein the second modification comprises an N-terminal methionyl residue and a coupling to polyethylene glycol.*

*15. A mutant hIL-4 protein according to claim 1 wherein the second modification consists of an N-terminal methionyl residue.*

*16. A mutant hIL-4 protein according to claim 13 wherein the second modification further comprises (i) the deletion of potential glycosylation sites; and/or (ii) the coupling of the protein to a non-protein polymer selected from the group consisting of polyethylene glycol, polypropylene glycol and polyoxyalkylenes.*

*17. A therapeutic composition comprising:*
   *a) a mutant hIL-4 protein according to any of claims 13, 14, 15 or 16; and*
   *b) a physiologically acceptable carrier.*

\* \* \* \* \*